(12) United States Patent
Andreucci et al.

(10) Patent No.: US 10,048,234 B2
(45) Date of Patent: Aug. 14, 2018

(54) ANALYZER FOR FLUIDS CONTAINING AN INFLAMMABLE SUBSTANCE AND CORRESPONDING METHOD

(75) Inventors: Phillipe Andreucci, Moirans (FR); Eric Colinet, Moirans (FR); Philippe Coric, Orvault (FR); Jean-Claude De Wit, Rueil Malmaison (FR); Pierre Puget, Saint-Isnier (FR)

(73) Assignees: Apix Analytics, Grenoble (FR); Total SA, Courbevoie (FR); EIF—Astute, Montreuil Sous Bois (FR)

( * ) Notice: Subject to any disclaimer, the term of this patent is extended or adjusted under 35 U.S.C. 154(b) by 566 days.

(21) Appl. No.: 14/405,000

(22) PCT Filed: Jun. 4, 2012

(86) PCT No.: PCT/FR2012/051241
§ 371 (c)(1),
(2), (4) Date: Mar. 30, 2015

(87) PCT Pub. No.: WO2013/182758
PCT Pub. Date: Dec. 12, 2013

(65) Prior Publication Data
US 2015/0300996 A1 Oct. 22, 2015

(51) Int. Cl.
*G01N 30/16* (2006.01)
*G01N 33/22* (2006.01)
(52) U.S. Cl.
CPC ............. *G01N 30/16* (2013.01); *G01N 33/22* (2013.01); *G01N 33/225* (2013.01)
(58) Field of Classification Search
CPC ...... G01N 33/225; G01N 33/22; G01N 30/16; G01N 33/227
See application file for complete search history.

(56) References Cited

U.S. PATENT DOCUMENTS 3,096,157 A 7/1963 Brown et al.
3,186,214 A 6/1965 Roberts
(Continued)

FOREIGN PATENT DOCUMENTS

FR          2812395 A1    2/2002
WO    WO 2011/154362 A1  12/2011

OTHER PUBLICATIONS

"Ultrasensitive nanoelectromechanical mass detection" by Ekinci et al., Appl. Phys. Lett. 84, 4469 (2004); doi: 10.1063/1.1755417, see attached publication.*

(Continued)

*Primary Examiner* — Paul West
*Assistant Examiner* — Xin Zhong
(74) *Attorney, Agent, or Firm* — Eric L. Lane; Green Patent Law

(57) ABSTRACT

Analyzer 1 for analyzing a fluid 3 containing at least one substance to be analyzed and at least one inflammable substance containing:
  a source of gas 9 to provide a flux of diluent gas,
  an injecting nozzle 11 for introducing samples of the fluid into the flux of diluent gas and for producing a gaseous flux, and
  a detector 7 for analyzing the gaseous flux,
wherein:
  the source of gas is intended to deliver a flux of diluent gas containing a material capable of supporting the combustion of the inflammable substance, preferably to deliver a flux of air,
  the injection nozzle is configured so as to introduce into the diluent gas samples of the fluid such that the average volume fraction of the fluid in the gaseous flux is less than $1/2{,}000$ and preferably less than $1/20{,}000$, and
(Continued)

the detector contains at least one microsensor for detecting the substance to be analyzed. Corresponding method.

17 Claims, 4 Drawing Sheets

(56) References Cited

U.S. PATENT DOCUMENTS

| | | | |
|---|---|---|---|
| 4,134,289 A | | 1/1979 | Bohl et al. |
| 4,351,614 A | * | 9/1982 | Garnier ................... G01N 25/54 374/37 |
| 4,632,572 A | | 12/1986 | Kude et al. |
| 4,799,394 A | | 1/1989 | Barnett et al. |
| 5,189,963 A | | 3/1993 | Mann |
| 5,231,865 A | | 8/1993 | McDermott et al. |
| 5,331,845 A | | 7/1994 | Bals et al. |
| 5,686,657 A | | 11/1997 | Craig et al. |
| 6,148,657 A | * | 11/2000 | Satoh ..................... G01N 30/88 422/84 |
| 6,351,983 B1 | * | 3/2002 | Haas ................... G01N 30/7206 250/281 |
| 6,450,011 B1 | | 9/2002 | Mayer et al. |
| 2003/0049854 A1 | | 3/2003 | Rhodes |
| 2005/0063865 A1 | | 3/2005 | Bonne et al. |
| 2006/0162425 A1 | | 7/2006 | Lange et al. |
| 2006/0292037 A1 | | 12/2006 | Favre et al. |
| 2007/0204749 A1 | | 9/2007 | Adkins |
| 2007/0212263 A1 | | 9/2007 | Shin et al. |
| 2007/0217993 A1 | | 9/2007 | Reimer et al. |
| 2007/0227602 A1 | | 10/2007 | Coric |
| 2009/0277655 A1 | | 11/2009 | DeCourcy et al. |
| 2010/0154519 A1 | | 6/2010 | Fontana |
| 2013/0192339 A1 | * | 8/2013 | Kriel ....................... G01N 1/22 73/23.36 |
| 2013/0333445 A1 | | 12/2013 | Andreucci et al. |

OTHER PUBLICATIONS

International Search Report and Opinion dated Apr. 3, 2013 in International Application No. PCT/FR2012/051241.

* cited by examiner

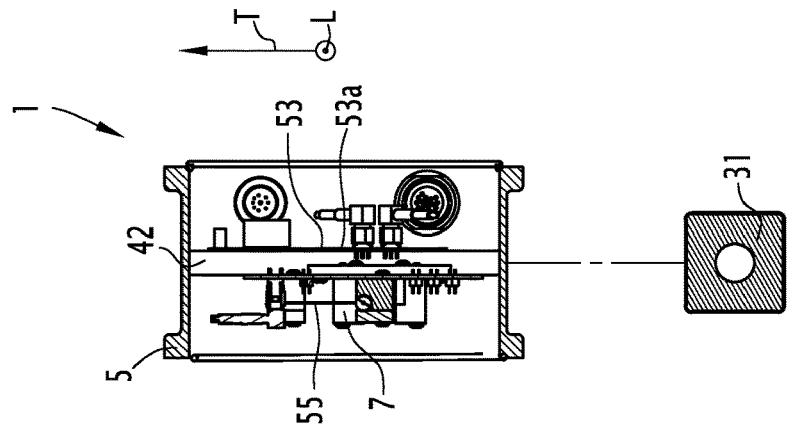
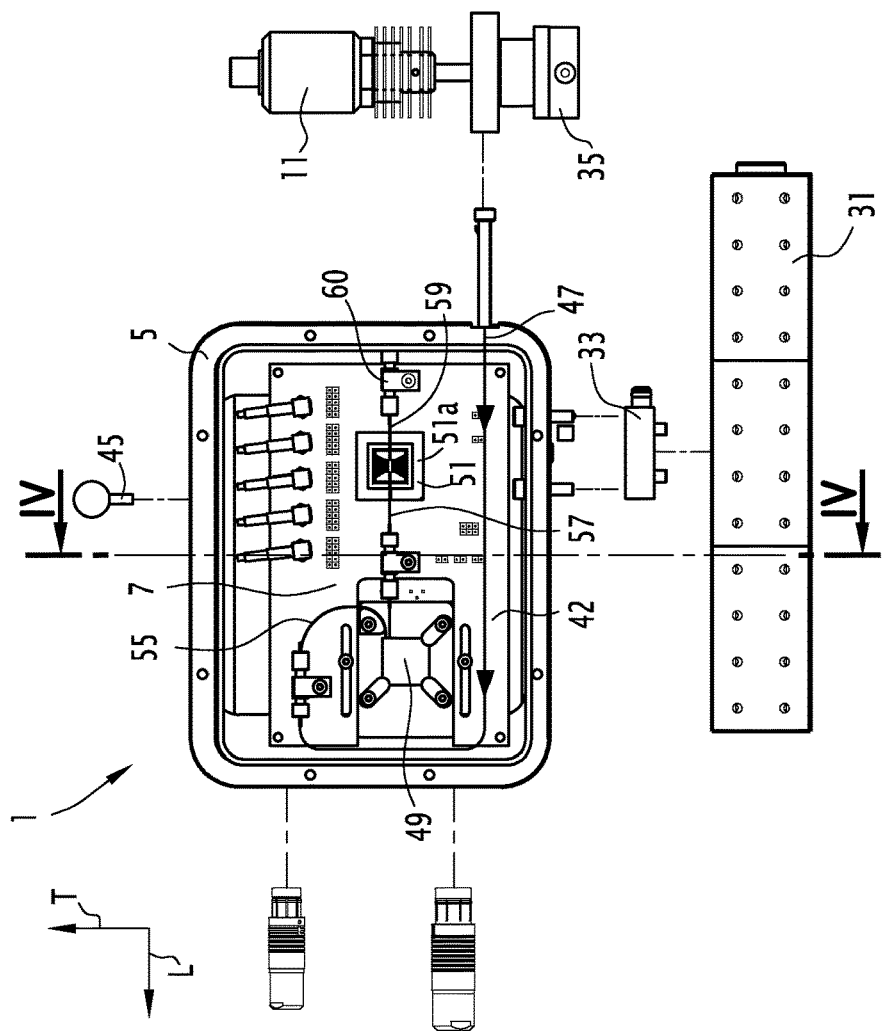
FIG.3
FIG.4

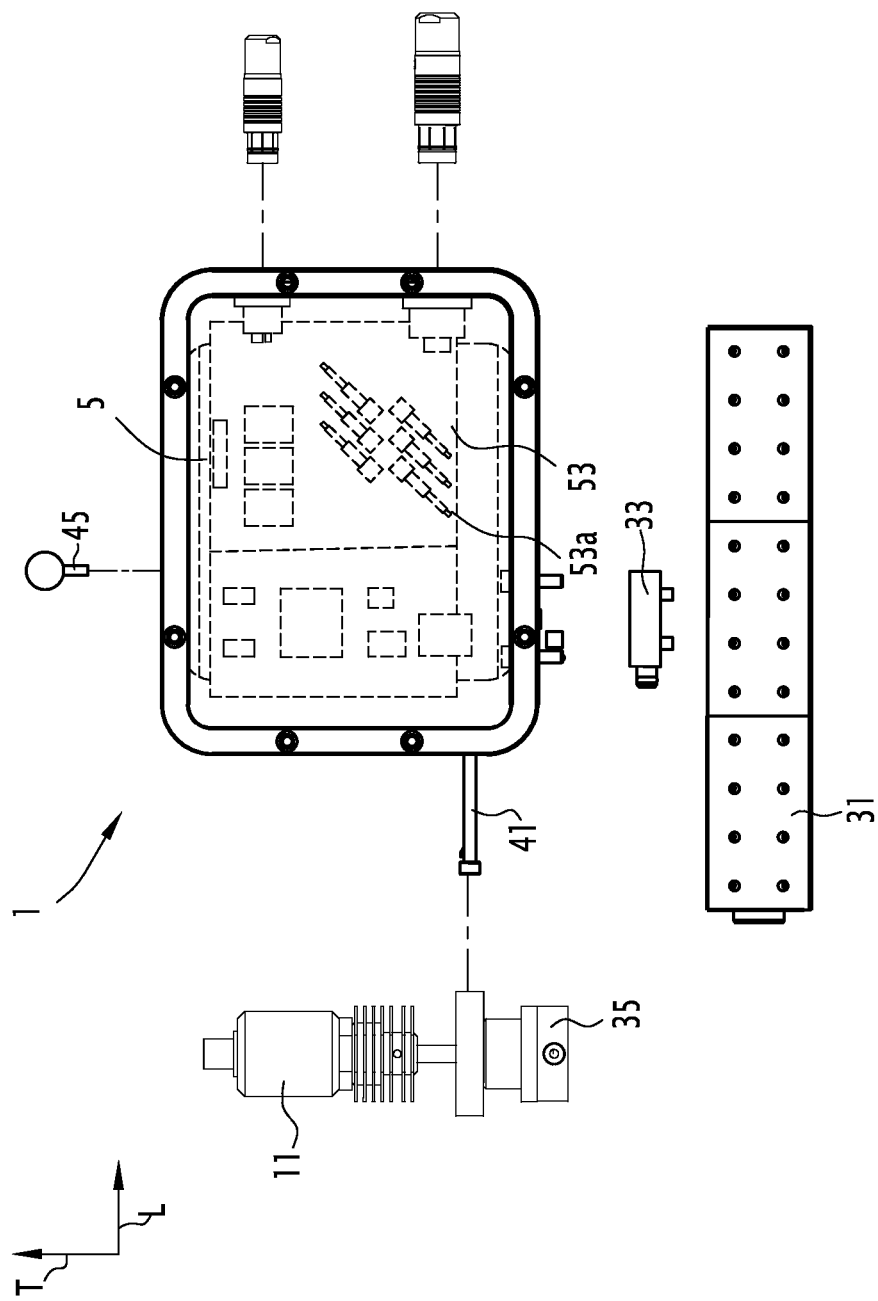

ANALYZER FOR FLUIDS CONTAINING AN INFLAMMABLE SUBSTANCE AND CORRESPONDING METHOD

BACKGROUND

The present invention relates to an analyzer of the kind capable of analyzing a fluid containing at least one substance to be analyzed and at least one inflammable substance, the analyzer containing:
a source of gas to provide a flux of diluent gas,
an injection nozzle for introducing samples of the fluid into the flux of diluent gas and producing a gaseous flux, and
a detector for analyzing the gaseous flux.

The invention also relates to a method for analyzing a fluid containing at least one substance to be analyzed, or an "analyte", and at least one inflammable substance which can be the analyte or some other substance.

The invention is more particularly adapted to the analysis of fluids presenting a risk of explosion or to an analysis performed in a potentially explosive atmosphere. For example, the invention is adapted to analyses carried out in the petroleum industry, chemistry and petrochemistry.

An explosive atmosphere, or "ATEX", is a mixture with air, under atmospheric conditions, of inflammable substances, for example in the form of a gas (methane, butane, propane, hydrogen . . . ) or of vapors (carbon disulfide, ethyl alcohol, ethylene oxide, acetone . . . ) in which, after inflammation, the combustion propagates to the unburned mixture.

The fluid to be analyzed can be liquid under the conditions under which it is removed but vaporizes in the diluent gas.

The mixture can become explosive if the concentration of the inflammable substance is above a lower explosivity limit (LEL) which is the minimum concentration of the inflammable substance in the mixture above which the mixture can be ignited. The LEL, often expressed in by volume of the inflammable substance in air, is of the order of 1% or of a few % for many analytes and about 0.5% for the most inflammable ones among them.

In the field of analyzers of the afore-said type, in order to avoid the risk of an explosion, it is known to use a diluent gas virtually free of oxygen, for example nitrogen obtained by cryogenic distillation, or hydrogen, or special mixtures not susceptible to ignite in contact with an analyte. Such a method has the advantage that the inflammation of the mixture of the diluent gas with the fluid to be analyzed is impossible regardless of the nature of the inflammable substance of the fluid to be analyzed or regardless of the mass of the samples of the fluid to be analyzed.

On the other hand, it is necessary to have at one's disposal a source of diluent gas, or gas of dilution, virtually free of oxygen and which in general has a non-negligible unit cost. Moreover, if the diluent gas virtually free of oxygen itself contains an inflammable substance such as hydrogen, the mixture to evacuate at the outlet from the analyzer itself presents a risk of explosion in case of contact with air or more generally with a substance supporting combustion.

One object of the invention is to provide an analyzer very well adapted to fluids containing at least one inflammable substance and that offers a more competitive cost of operation.

SUMMARY

To this end, the invention has for an object an analyzer of the afore-described type in which:

the source of gas is intended to deliver a flux of diluent gas containing a substance supporting combustion of the inflammable substance, preferably so as to deliver a flux of air,
the injection nozzle is configured so as to introduce into the flux of diluent gas samples of fluid such that the average volume fraction of the fluid in the gaseous flux is below $1/2,000$ and preferably below $1/20,000$, and
the detector contains at least one microsensor for detecting the substance to be analyzed.

By "analyze the fluid" is meant optionally the act of measuring one or more parameters representative of the mass fraction of the substance to be analyzed in the fluid or simply the act of detecting the presence of the substance to be analyzed in the fluid.

By "A is connected fluidically to B" is meant that there exists a connection between elements A and B that allows the routing of a fluid, for example a conduit or capillary tube. The connection may contain elements such as control valves, pump, sensor or derivations thereof.

By "average volume fraction of the fluid in the gaseous flux" is meant the average fraction of the fluid in the gaseous flux in time taking into account the fact that the samples of the fluid are injected in a discrete manner. In other words, the volume of the injected samples is divided by the volume of the gaseous flux injected during a certain time period, sufficient for the average obtained not to depend on the time period chosen. If the sample injection is cyclic, this time period corresponds to a whole number of periods of the injection cycle.

The substance to be analyzed can be the inflammable substance in question or it can be some other substance. There can be several inflammable substances in the fluid to be analyzed.

According to particular embodiments, the analyzer can have one or more of the following characteristics taken separately or in all technically possible combinations:
the injection nozzle is capable of introducing, preferably in cyclic manner, into the flux of diluent gas samples of fluid each weighing less than 10 nanograms and preferably less than 1.5 nanograms;
the detector is located in a box;
the analyzer contains means for injecting into the box a flux of sweeping gas, the box being provided with an evacuation outlet for evacuating the flux of purge gas, the means of injecting the flux of purge gas and the evacuation outlet being capable of maintaining inside the box an overpressure relative to the outside of the box;
the means for injecting the flux of purge gas are connected fluidically to the source of gas so as to inject the diluent gas as the purge gas;
the means for injecting the flux of purge gas are configured so as to inject the flux of purge gas into the box at a flow rate higher than 5 times the average flow rate of the gaseous flux and preferably higher than or equal to 9 times the average flow rate of the gaseous flux;
the analyzer comprises a modular interface on which the box and the injection nozzle are fixed, the modular interface being intended to receive at the inlet the fluid so as to route the fluid toward the injection nozzle and being connected to the source of gas in order to, optionally, route the flux of the flow gas to the box and/or route the flux of the diluent gas to the injection nozzle;
the detector comprises an outlet to set free, after analysis or no analysis, at least a fraction and preferably the totality of the gaseous flux inside the box;

the detector contains an electronic control card, the microsensor, the electronic card each comprising a packing to prevent the appearance of a spark inside the box;

the source of gas contains a purifier;

the detector contains a chromatographic microcolumn.

The invention also relates to a method of analyzing a fluid containing at least one substance to be analyzed and at least one inflammable substance, the method comprising at least the following steps:

a) obtaining a flux of diluent gas from a source of gas, b) introducing into the flux of diluent gas samples of the fluid to produce a gaseous flux, and c) analyzing the gaseous flux in a detector, wherein:

in step a) the flux of diluent gas comprises a substance capable of supporting the combustion of the inflammable substance and preferably a flux of air, in step b) the samples are such that the average volume fraction of the fluid in the gaseous flux is less than $1/2,000$ and preferably less than $1/20,000$ and in step c) the detector is at least a microsensor for detecting the substance to be analyzed.

According to particular embodiments, the method may comprise one or more of the following characteristics taken individually or in any technically possible combination:

in step b) each of the samples of the fluid introduced into the flux of diluent gas weighs less than 10 nanograms and preferably less than 1.5 nanograms;

in step c) the detector is located in a box into which is injected a flux of purge gas, the flux of sweeping gas maintaining an overpressure, the flux of purge gas escaping from the box through at least one evacuation outlet, the injection of the flux of the purge gas maintaining inside the box an overpressure relative to the outside of the box;

in step c) the box has an internal volume and the injection of the flux of purge gas is carried out at a rate and temperature such that no point of any wall delimiting the internal volume of the box has a temperature higher than or equal to 85° C.;

in step c) the detector contains a chromatographic microcolumn.

BRIEF DESCRIPTION OF THE DRAWINGS

The invention will be better understood by reading the following description, given only as an example, and by reference to the attached drawings in which:

FIG. 3 represents schematically a front view, partly blown up, of the device shown in FIG. 2, FIG. 4 represents schematically a transverse view the part of the device shown in FIGS. 2 and 3, and FIG. 5 represents schematically a back view, partly blown up, of the part of the device shown in FIGS. 2 and 3.

DETAILED DESCRIPTION

Figure 1:
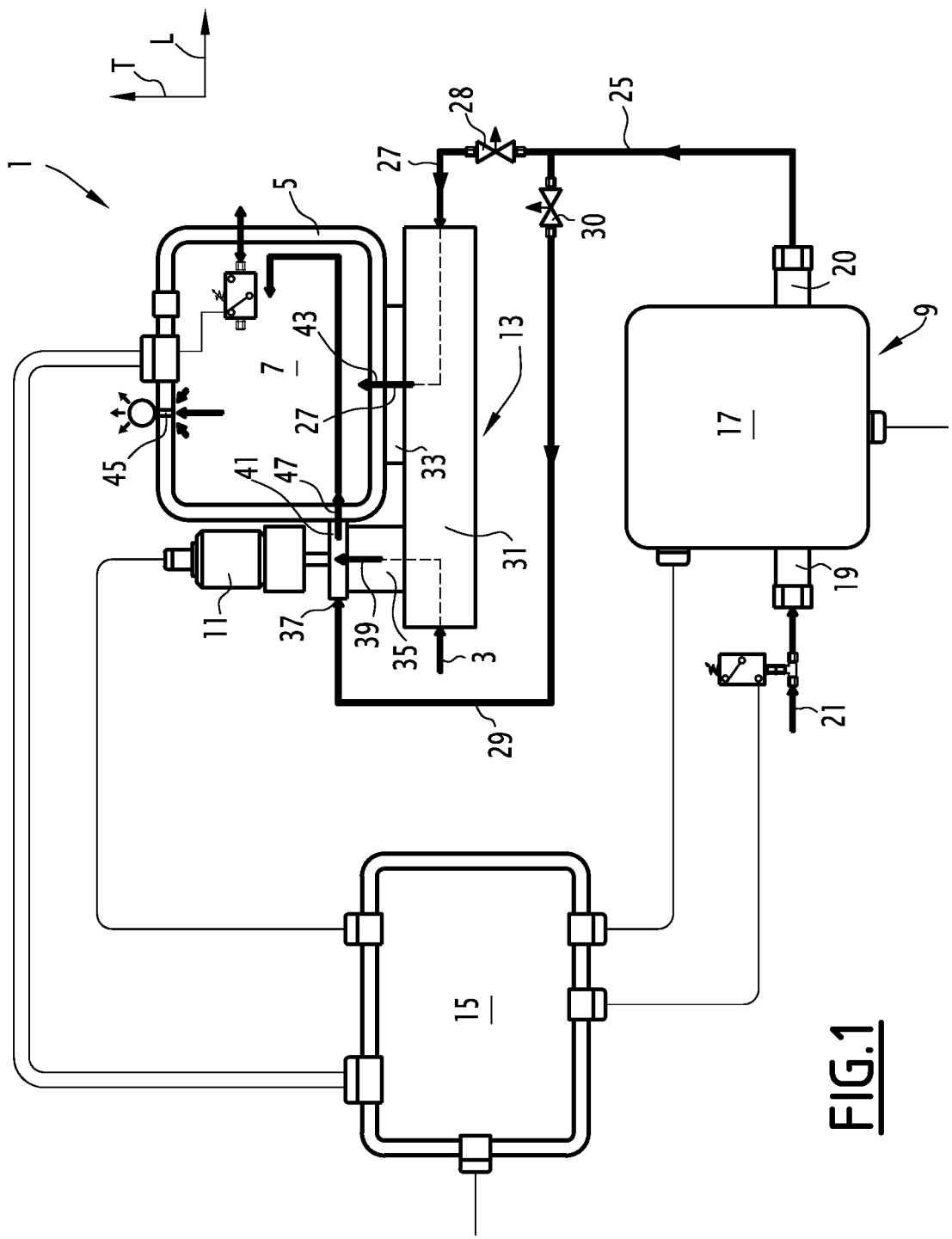
FIG. 1 represents schematically a device according to the invention, with the interior of the box not shown in detail.
Figure 2:
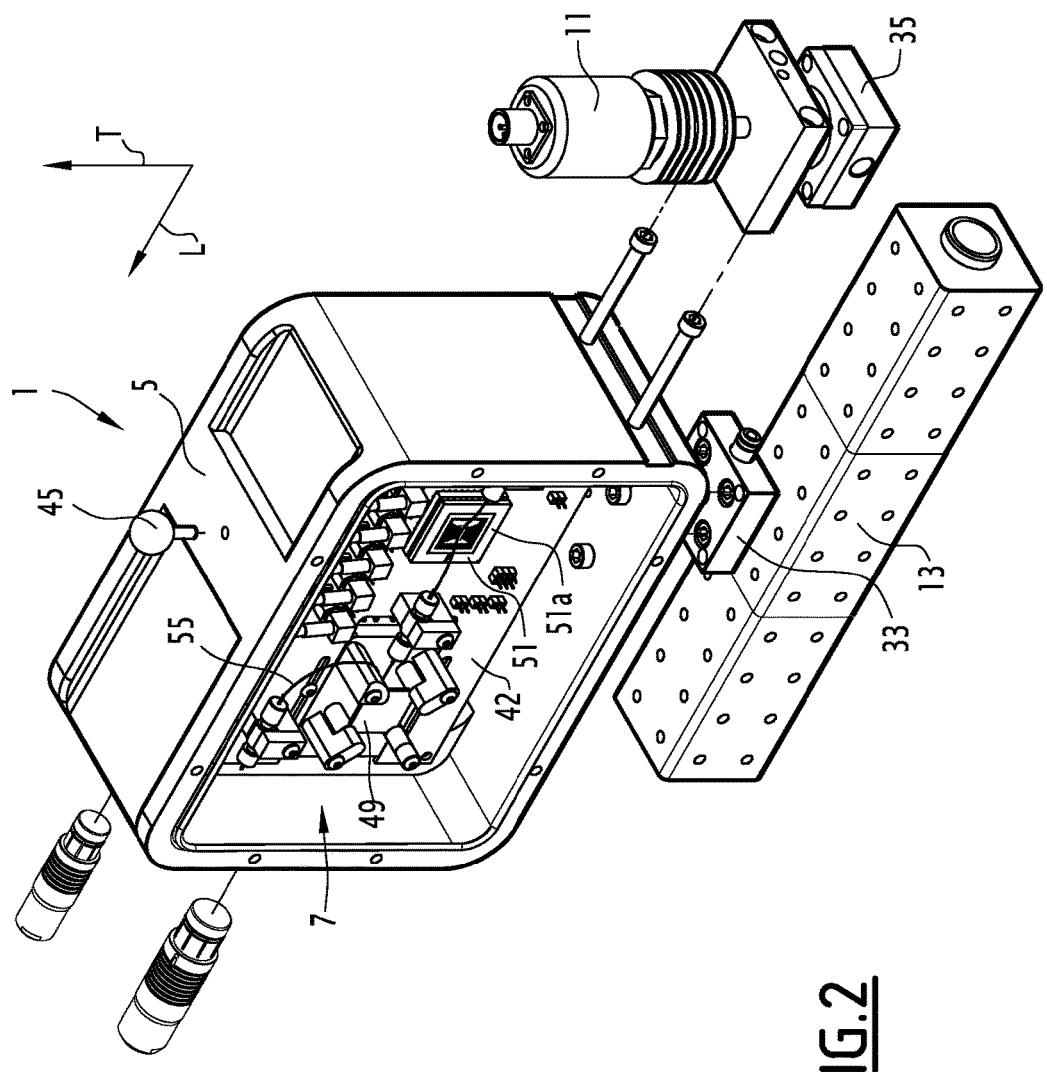
FIG. 2 represents schematically in perspective a part of the device shown in FIG. 1.

An analyzer 1 according to the invention is described by reference to FIGS. 1 to 5. Analyzer 1 is intended, for example, to analyze a fluid 3 stemming from a petroleum refinery.

Fluid 3 is, for example, a mixture of gas produced by a petrochemical method, the gas mixture comprising a substance to be analyzed, for example benzene. Benzene is an inflammable substance having an LEL of 1.2%.

The analyzer (FIG. 1) comprises a box 5, a detector 7 located in box 5, a source of air 9 and an injection nozzle 11 connected fluidically at the intake to the source of air 9 and receiving the fluid 3 to be analyzed, injection nozzle 11 being connected at the outlet to detector 7 through box 5. Analyzer 1 contains advantageously a modular interface 13 on which are mounted box 5 and injection nozzle 11.

Analyzer 1 additionally contains an assembly 15 for feeding arid controlling the source of air 9, injection nozzle 11 and detector 7.

The source of air 9 contains advantageously a purifier 17 comprising an inlet route 19 connected to an instrument air line 21 and an outlet route 20 for the purified air connected to an air duct 25.

Purifier 17 is, for example, a Parker Balston 75-82EU air generator capable of removing the hydrocarbons possibly present in the instrument air 21 and of reducing their overall concentration to less than 0.1 ppm.

As a variant, the source of air can be the atmosphere, the atmospheric air preferably being filtered.

Air duct 25 has a first branch 27 for conducting a flux of sweeping air into box 5 via modular interface 13. The first branch 27 contains a valve 28 for controlling the flux rate of the sweeping air.

By "gas flux" is meant the displacement of a gas by forced convection and to which can be associated a rate that characterizes the intensity of the flux.

Air duct 25 has a second branch 29 for conducting a flux of diluent gas toward injection nozzle 11. Second branch 29 has a valve 30 for controlling the flux rate of the diluent gas.

Modular interface 13 comprises several intakes and several outlets and makes it possible to connect fluidically each intake to one or more outlets.

Modular interface 13 is advantageously analogous to the assembly described in patent application WO-A-2007110504.

Modular interface 13 is sometimes called "Nessi", namely conforming to standard ISA SP 76, and permits the interoperability between different components supplied by different manufacturers and the interchangeability of said components.

Modular interface 13 advantageously contains a body 31 extending in a longitudinal direction L, a conducting module 33 for the sweeping of air and for fixing box 5 on body 31 and a module 35 for conducting fluid 3 and for fixing injection nozzle 11 on body 31.

Body 31 is analogous to the body (reference 3) of the assembly described in WO-A-2007110504.

Module 33 is analogous to a module (reference 5) of the assembly described in WO-A2007110504, box 5 of the present invention playing the role of one of the functional components (reference 7) of WO-A-2007110504.

Module 35 is analogous to another module (reference 5) of the assembly described in WO-A-2007110504, injection nozzle 11 of the present invention playing the role of one of the functional components (reference 7) of WO-A-2007110504.

A transverse direction T perpendicular to the longitudinal direction L is also defined. For example, direction T is vertical, as shown in the figures.

Injection nozzle 11 extends, for example, along transverse direction T starting from modular interface 13.

Injection nozzle 11 comprises a first inlet 37 fluidically connected to the second branch 29 to receive the flux of diluent gas, a second inlet 39 connected to module 35 to receive fluid 3 and an outlet 41 for a gaseous flux resulting from the introduction of samples of fluid 3 into the flux of diluent gas, outlet 41 being connected fluidically to detector 7.

Injection nozzle 11 is provided for introducing into the diluent gas, for example cyclically, a calibrated amount of fluid 3 advantageously of less than 10 ng (nanograms) and preferably of less than 1.5 ng.

Advantageously, injection nozzle 11 is a ROLSI™-type valve which is described in the document FR-A-2 853 414.

Box 5 forms a cabinet advantageously meeting the requirements of European ATEX standard, namely it is capable of protecting its contents, particularly detector 7, from explosions that could take place around box 5. For example, the cabinet is capable of being pressurized to a pressure of 50 Pa above the pressure prevailing around box 5.

For example, box 5 has a virtually parallelepipedic general shape. Box 5 extends, for example, along transverse direction T starting from modular interface 13.

Advantageously, box 5 comprises an internal plate 42 which, for example, extends virtually parallel to longitudinal direction L and transverse direction T and serves to support detector 7.

Box 5 has an intake 43 for the sweeping gas, a vent 45 for evacuating the gas contained in box 5 and an intake 47 for the gaseous flux intended for detector 7.

Vent 45 is capable of maintaining in box 5 an overpressure advantageously comprised between 50 and 200 Pa. For example, vent 45 ensures a permanent and controlled purge so as to maintain a pressure loss between the inside of box 5 and the outside of box 5 equal to the overpressure desired, for example one equal to 50 Pa.

Vent 45 advantageously contains a flame-arresting system to prevent the propagation of a combustion from the exterior of box 5 toward the interior of box 5.

Detector 7 (FIGS. 2, 3 and 4) extends on the two faces of plate 42. Detector 7 comprises a chromatographic microcolumn 49, a microsensor 51 and an electronic card 53.

Chromatographic microcolumn 49 is, for example, of the kind embossed on silicon. Chromatographic microcolumn 49 is, for example, analogous to the one described in document WO-A-2011/154362, particularly on page 11, line 16 and on page 12, line 20. Chromatographic microcolumn 49 is of the microcapillary type with a diameter between, for example, 10 µm and a few hundred µm. In the "unfolded" state, chromatographic microcolumn 49 has, for example, a length between 0.5 m and a few meters. Chromatographic microcolumn 49 is internally coated with a film of material referred to as "stationary phase".

The film is applied by methods known to those skilled in the art. The film consists, for example, of a polymer such as polyethylene glycol or polydimethylsiloxane. The film is a solid, a gel or a liquid.

Chromatographic microcolumn 49 is advantageously fixed on plate 42. At the intake, chromatographic microcolumn 49 is connected by a capillary tube 55 to the intake 47 of box 5 to receive the gaseous flux to be analyzed and coming from outlet 41 of injection nozzle 11. At the outlet, chromatographic microcolumn 49 is connected by a capillary tube 57 to microsensor 51 so that the gaseous flux can be sent to microsensor 51.

Microsensor 51 is, for example, of the NEMS type (in English NEMS=nano electromechanical system). It is for example of the type described in document WO-A-2011/154362, particularly on pages 12 to 15. In the example shown, microsensor 51 is located at the outlet from the chromatographic microcolumn 49. Microsensor 51 is advantageously fixed on plate 42 on the same side as chromatographic microcolumn 49.

Microsensor 51 advantageously comprises at least one microsensor for the substance to be analyzed. By "microsensor" is meant a sensor the useful surface of which amounts to about 100 $nm^2$ to a few $\mu m^2$.

Microsensor 51 is, for example, of the gravimetric type. It has a vibrating surface capable of detecting and quantifying molecules of the substance to be analyzed.

Microsensor 51 is, for example, of the type described by Whiting, J. J., C. S. Fix, J. M. Anderson et al. in "*High-speed two-dimensional gas chromatography using microfabricated GC columns combined with nanoelectromechanical mass sensors*" presented at TRANSDUCERS 2009-15$^{th}$ International Conference on Solid-State Sensors, Actuators and Microsystems, 2009.

Advantageously, microsensor 51 contains a packing 51a capable of preventing a spark from forming inside box 5 starting from microsensor 51. Packing 51a, for example, meets the requirements of standard EN 60079.

According to one variant, not represented, microsensor 51 can be located inside chromatographic microcolumn 49. According to another variant, not represented, there could be several distinct microsensors 51 located optionally at the outlet and/or at different points of chromatographic microcolumn 49, advantageously on an internal wall of chromatographic microcolumn 49. According to another advantageous variant, a network of microsensors 51 can be disposed from the intake of chromatographic microcolumn 49 to its outlet.

A capillary tube 59 is connected to an outlet from microsensor 51 for the evacuation of the gaseous flux from the interior of the box 5 via a diffuser 60.

Electronic card 53 is advantageously fixed on the other side of plate 42 relative to chromatographic microcolumn 49 and microsensor 51. Electronic card 53 is connected electrically to chromatographic microcolumn 49 and to microsensor 51 so as to feed and control chromatographic microcolumn 49 and microsensor 51 and to acquire electric measurement signals coming from microsensor 51.

Electronic card 53 advantageously contains a packing 53a capable of preventing the formation of a spark developing from electronic card 53 inside box 5. Packing 53a meets the requirements of, for example, standard EN 60079, part 18.

Assembly 15 contains automatic systems and interlocks known to those skilled in the art.

The functioning of analyzer 1 will now be described.

Instrument air 21 (FIG. 1) enters the purifier 17 through intake 19. Purifier 17 is supplied electrically and controlled by assembly 15. Purifier 17 purifies the instrument air and sends a flux of purified air to air duct 25.

The flux of purified air is divided in the first branch 27 into a flux of sweeping air and in branch 29 into a flux of diluent air. Control valves 28, 30 make it possible to control selectively the flux rates of the sweeping air and diluent gas.

Advantageously, the flux rate of the diluent gas is comprised between 0.1 and 3 ml/min. It is, for example, about 1 ml/minute. The flux of the diluent gas before its entry into box 5 is, for example, at a pressure of about 50 Pa above ambient pressure and, for example, at ambient temperature.

The flux rate of the sweeping air in box 5 is advantageously higher than 5 times the rate of the flux of diluent gas. For example, it is about 9 times that of the flux of the diluent gas or about 9 ml/minute. The flux of the sweeping air before it enters box 5 is, for example, at a pressure of about 50 Pa above ambient pressure and for example at ambient temperature.

The flux of sweeping air passes into body 31 of modular interface 13 and into module 33 and enters box 5 through intake 43. The flux of sweeping air then sweeps the inside of box 5 and exits through vent 45. The sweeping advantageously takes place on both sides of plate 42.

Advantageously, the injection of the flux of sweeping gas takes place at a temperature such that no wall delimiting the internal volume of box 5 has a point presenting a temperature higher than or equal to 85° C. in order to reduce the risks of inflammation of the gases present inside box 5.

The flux of diluent gas arrives at the first intake 37 of injection nozzle 11.

The fluid to be analyzed, i.e. fluid 3, passes into body 31 and the modular interface 13, and then part of fluid 3 arrives at the second intake 39 of injection nozzle 11 via module 35.

Injection nozzle 11 is supplied electrically and is controlled by assembly 15. Injection nozzle 11 introduces samples of fluid 3 arriving through second intake 39 into the diluent gas arriving through the first intake 37 and produces a gaseous flux that exits through outlet 41.

Injection nozzle 11 brings about a dilution of fluid 3 by the diluent gas. The dilution brings the volume fraction of all constituents of the gaseous flux resulting from fluid 3 to below $1/2,000$ and preferably below $1/20,000$. In other words, the dilution brings the volume fraction of all constituents of the gaseous flux resulting from fluid 3 to at least one order of magnitude and preferably two orders of magnitude below 0.5%, i.e., below the LEL of the most constraining inflammable substances.

For example, injection nozzle 11 introduces into the flux of diluent gas once per minute a sample advantageously weighing less than 10 ng and for example 1 ng, which ensures that the average volume fraction of fluid 3 in the gaseous flux is less than $1/2,000$.

The gaseous flux containing fluid 3 thus diluted enters box 5 through intake 47 (FIG. 3) and arrives by capillary tube 55 to the intake of chromatographic microcolumn 49. Chromatographic microcolumn 49 separates the substances contained in the gaseous flux by differential migration as a function of their respective affinities to the stationary phase, each substance possessing a migration rate that depends on its affinity to the stationary phase.

The gaseous flux then exits from chromatographic microcolumn 49 through capillary tube 57 and arrives in microsensor 51.

Microsensor 51 detects the presence of the substance to be analyzed and/or measures the quantity of the substance to be analyzed in the gaseous flux that traverses it.

Microsensor 51 measures a variation of the parameters that characterize the vibration of the vibrating surface, for example the frequency of resonance of the vibrating surface.

To create this resonance, electronic card 53 excites microsensor 51 to a particular frequency. Electronic card 53 measures the electric signals created by this resonance and processes them or sends them to a distant terminal. The signals of microsensor 51 are in general analog, of low level (of the order of one mV) and of high frequency (from about ten megahertz to a few hundred megahertz).

To minimize the perturbation of these signals by external electromagnetic fields, it is useful to minimize the length of the electric connections between microsensor 51 and electronic card 53. It is therefore advantageous to locate electronic card 53 in box 5.

The gaseous flux, after it has passed into microsensor 51, makes use of capillary tube 59 and is released into box 5 via element 60. The gaseous flux then blends with the flux of sweeping air thus creating a new dilution of about one order of magnitude of inflammable substances contained in the gaseous flux.

As a result of the characteristics of analyzer 1 described in the foregoing, fluid 3 although containing at least one inflammable substance is brought into contact with air as the diluent gas without the risk of explosion, because the dilution has brought the average volume fraction of all substances contained in the gaseous flux to values one to two orders of magnitude below the most constraining LEL values. Such dilution is possible because detector 7 contains a chromatographic microcolumn 49 and a microsensor 51 that permit the separation and detection of the substance to be analyzed at a very low concentration.

Thus, detector 7 makes it possible to analyze the substance to be analyzed in spite of its considerable dilution. Analyzer 1 is thus well suited for fluids containing at least one inflammable substance such as fluid 3. Since analyzer 1 uses air as the diluent gas, its operating cost is more competitive than if it used a special gas such as nitrogen.

Microsensor 51 being of the NEMS type and chromatographic microcolumn 49 being embossed on silicon make it possible to introduce into the flux of diluent gas samples of fluid 3 of reduced weight, for example of about 1 ng, which reduces even more the risk of explosion of the gaseous flux sent to detector 7.

In addition, the optional characteristics according to which the sweeping of air is performed in box 5 and the mixing of the flux of sweeping air after analysis takes place in detector 7 make it possible, advantageously, to dilute the inflammable substances in box 5 even more.

The dilution of fluid 3 in the gaseous flux presents the additional advantage that if toxic substances are present in fluid 3, very low amounts of these toxic substances are released by device 1.

According to a variant that is not represented, injection nozzle 11 and/or air purifier 17 can be situated inside box 5 so as to profit from the protection against explosive atmospheres provided by box 5.

The invention claimed is:

1. An analyzer for analyzing a fluid containing at least one substance to be analysed and at least one inflammable substance, the analyzer containing:
   a source of gas to provide a flux of diluent gas,
   an injecting nozzle for introducing samples of the fluid into the flux of diluent gas and producing a gaseous flux,
   a detector for analyzing the gaseous flux, the detector being located in a box, and
   a modular interface on which the box and the injecting nozzle are fixed, the modular interface being:
   intended to receive at an intake the fluid so as to route the fluid toward the injection nozzle, and
   connected to the source of gas so as to route a flux of purge gas to the box and/or to route the flux of diluent gas to the injection nozzle,
   wherein:
   the source of gas is intended to deliver a flux of diluent gas containing a substance supporting combustion of the inflammable substance,
   the injecting nozzle is configured so as to introduce into the flux of diluent gas samples of the fluid such that an average volume fraction of the fluid in the gaseous flux is below $1/2,000$, the detector contains at least one microsensor for detecting the substance to be analysed, and the analyser contains means for injecting the flux of purge gas into the box, the box being provided with an evacuation outlet for evacuating the flux of purge gas, the means of injection of the flux of purge gas and the evacuation outlet being capable of maintaining inside the box an overpressure relative to the outside of the box.

2. The analyzer according to claim 1, wherein the injecting nozzle is capable of introducing into the flux of diluent gas, samples of the fluid each weighing less than 10 nanograms.

3. The analyzer according to claim 1, wherein the means of injecting the flux of purge gas are connected fluidically to the source of gas so as to inject the diluent gas as the purge gas.

4. The analyzer according to claim 1, wherein the means for injecting the flux of purge gas are configured so as to inject the flux of purge gas into the box at a flow rate higher than 5 times an average flow rate of the gaseous flux.

5. The analyzer according to claim 1, wherein the detector has an outlet to set free, after analysis, at least a fraction of the gaseous flux inside the box.

6. The analyzer according to claim 1, wherein the detector contains an electronic control card, the microsensor and the electronic card each being provided with a packing to prevent the forming of a spark inside the box.

7. The analyzer according to claim 1, wherein the source of gas contains a purifier.

8. A method for analyzing a fluid containing at least one substance to be analyzed and at least one inflammable substance, the method comprising providing an analyzer according to claim 1 and at least the following steps:

a) obtaining a flux of diluent gas from a source of gas,
b) introducing into the flux of diluent gas samples of the fluid to produce a gaseous flux, and
c) analyzing the gaseous flux in a detector,
wherein:
in step a) the flux of diluent gas contains a material capable of supporting the combustion of the inflammable substance, said material being a flux of air,
in step b) the samples are such that the average volume fraction of the fluid in the gaseous flux is less than $1/2,000$, and
in step c) the detector is at least a microsensor detecting the substance to be analyzed.

9. The method according to claim 8, in which, in step b), each of the samples of the fluid introduced into the flux of diluent gas weighs less than 10 nanograms.

10. The method according to claim 8, wherein in step c) the detector is located in a box into which is injected a flux of purge gas, the purge gas leaving the box through at least one evacuation outlet, the injection of the flux of purge gas maintaining an overpressure inside the box relative to the outside of the box.

11. The method according to claim 10, wherein in step c), the box presenting an internal volume, the injection of the purge gas takes place at a flow rate and temperature such that on no wall delimiting the internal volume of the box there is a point presenting a temperature higher than or equal to 85° C.

12. The analyzer according to claim 1, wherein the injecting nozzle is configured so as to introduce into the flux of diluent gas samples of the fluid such that the average volume fraction of the fluid in the gaseous flux is below $1/20,000$.

13. The analyzer according to claim 2, wherein the injecting nozzle is capable of introducing into the flux of diluent gas, samples of the fluid each weighing less than 1.5 nanogram.

14. The analyzer according to claim 2, wherein the injecting nozzle is capable of introducing into the flux of diluent gas in a cyclical manner.

15. The analyzer according to claim 1, wherein the detector has an outlet to set free, after analysis, the totality of the gaseous flux inside the box.

16. The method according to claim 8, wherein in step b) the samples are such that the average volume fraction of the fluid in the gaseous flux is less than $1/20,000$.

17. The method according to claim 9, wherein, in step b), each of the samples of the fluid introduced into the flux of diluent gas weighs less than 1.5 nanogram.

* * * * *